(12) United States Patent
Couturier et al.

(10) Patent No.: US 8,779,213 B2
(45) Date of Patent: Jul. 15, 2014

(54) BIO-BASED GLUTARALYDEHYDE, AND MANUFACTURE METHODS THEREOF

(75) Inventors: Jean Luc Couturier, Lyons (FR); Jean Luc Dubois, Millery (FR)

(73) Assignee: Arkema France, Colombes (FR)

( * ) Notice: Subject to any disclaimer, the term of this patent is extended or adjusted under 35 U.S.C. 154(b) by 0 days.

(21) Appl. No.: 13/505,811

(22) PCT Filed: Oct. 19, 2010

(86) PCT No.: PCT/FR2010/052215
§ 371 (c)(1),
(2), (4) Date: Jul. 10, 2012

(87) PCT Pub. No.: WO2011/055051
PCT Pub. Date: May 12, 2011

(65) Prior Publication Data
US 2012/0277475 A1    Nov. 1, 2012

(30) Foreign Application Priority Data
Nov. 4, 2009  (FR) ...................................... 09 57795

(51) Int. Cl.
*C07C 45/29*    (2006.01)
*C07C 45/60*    (2006.01)

(52) U.S. Cl.
USPC ............................ 568/471; 568/483; 568/494

(58) Field of Classification Search
USPC ......................................... 568/471, 483, 494
See application file for complete search history.

(56) References Cited

U.S. PATENT DOCUMENTS 7,396,962 B1 *   7/2008  Dubois et al. ................. 568/485

FOREIGN PATENT DOCUMENTS

WO     WO 99/23088 A1    5/1999

OTHER PUBLICATIONS

International Search Report of PCT/FR2010/052215 (Apr. 21, 2011).
M.J. Antal et al., "Pyrolytic Sources of Hydrocarbons from Biomass", Journal of Analytical and Applied Pyrolysis, vol. 8 (1985) pp. 291-303.
A. Miyata et al., "Catalytic Aerobic Oxidation of Diols Under Photo-Irradiation: Highly Efficient Synthesis of Lactols", Tetrahedron Letters, vol. 43, No. 19 (2002) pp. 3481-3484.
W.E. Kaufmann et al., "The Use of Platinum Oxide as a Catalyst in the Reduction of Organic Compounds. IV. Reduction of Furfural and its Derivatives", Journal of the American Chemical Society, vol. 45, No. 12 (Dec. 1923) pp. 3029-3044.
G.A. Adams et al., "Conversion of Xylose to Furfural by Means of Hydrobromic Acid", Canadian Journal of Research, vol. 26b, No. 3 (1948) pp. 309-313.
R. Singh et al., "Mechanism of Ruthenium(III)-Catalysed Oxidation of Butane-1,4-diol and Pentane-1,5-diol by Alkaline Hexacyanoferrate(III)", Journal of Chemical Research, vol. 10 (1977) p. 249.

* cited by examiner

*Primary Examiner* — Sikarl Witherspoon
(74) *Attorney, Agent, or Firm* — Millen, White, Zelano & Branigan, P.C.

(57) ABSTRACT

The present invention relates to a bio-based glutaraldehyde compound and to the different non-fossil, natural raw material manufacture methods thereof. To prepare said compound, glycerol created by the methanolysis of vegetable oil or animal fat is used, leading after dehydration to acrolein that is caused to react with a vinyl/alkyl/ether as per a Diels-Alder cyclization reaction, followed by hydrolysis so as to obtain the bio-based glutaraldehyde of the invention. Sugars containing five carbon atoms, that is, pentoses created from for example hemicellulose, may also be used, leading after dehydration to furfural, which leads, after complete hydrogenation followed by selective oxidation, to the bio-based glutaraldehyde of the invention.

20 Claims, No Drawings

BIO-BASED GLUTARALYDEHYDE, AND MANUFACTURE METHODS THEREOF

The present invention relates to a pentane-1,5-dial compound, usually referred to as glutaraldehyde, which is bio-sourced, and also to various manufacturing processes for the same.

Glutaraldehyde is a synthetic chemical compound of formula CHO—$(CH_2)_3$—CHO which has been known for a very long time.

The standard preparation of this compound is performed from acetylene, ethanol and acrolein in a three-step process consisting in a first step in reacting acetylene and ethanol to obtain vinyl ethyl ether, and then in reacting the latter with acrolein according to a Diels-Alder cyclization mechanism to obtain a pyran compound, 2-ethoxy-3,4-dihydropyran, which is finally subjected to a hydrolysis leading to glutaraldehyde. The same process may be performed using methanol instead of ethanol. This process is especially described in Chinese patents 1358704 and 1526691 and patent application WO 99/23088.

Glutaraldehyde is used in many applications, such as leather tanning, the impermeabilization of papers and textiles and the sterilization of medical surfaces and equipment in hospitals, tissue storage, embalming, the preparation of supported enzymes, and the crosslinking of proteins and of polyhydroxy compounds.

The process described above, in particular that described in document WO 99/23088, which is the main process for producing glutaraldehyde, is based on the use of fossil hydrocarbon raw materials: acetylene and acrolein whose industrial synthesis is performed by oxidation of propylene and/or propane. These raw materials are derived from petroleum or natural gas, and, consequently, glutaraldehyde is constituted from non-renewable fossil carbon-based raw materials. In addition, the processes for extracting, purifying and synthesizing the raw materials and also the processes for destroying at the end of the cycle the manufactured finished products based on these fossil raw materials generate carbon dioxide, the latter also being a direct byproduct of the oxidation reactions of propylene to acrolein. All this contributes towards increasing the concentration of greenhouse gases in the atmosphere. In the context of the undertakings by many of the industrialized countries to reduce the emissions of greenhouse gases, it appears particularly important to manufacture novel products based on renewable raw materials that contribute towards reducing these environmental effects.

The invention is directed towards overcoming these drawbacks by preparing a bio-sourced glutaraldehyde compound. The term "bio-sourced glutaraldehyde compound" means a compound with a $^{14}C$ carbon content characteristic of the non-fossil natural origin of the raw materials used.

The use of carbon-based raw materials of natural and renewable origin may be detected by means of the carbon atoms included in the composition of the final product. Specifically, unlike materials derived from fossil matter, materials composed of renewable raw materials contain $^{14}C$. All the carbon samples taken from live organisms (animals or plants) are in fact a mixture of three isotopes: $^{12}C$ (representing ~98.892%), $^{13}C$ (~1.108%) and $^{14}C$ (traces: $1.2 \times 10^{-10}$%). The $^{14}C/^{12}C$ ratio of living tissue is identical to that of the atmosphere. In the environment, $^{14}C$ exists in two predominant forms: in mineral form, i.e. carbon dioxide ($CO_2$), and in organic form, i.e. carbon incorporated into organic molecules.

In a live organism, the $^{14}C/^{12}C$ ratio is kept constant by the metabolism, since the carbon is continuously exchanged with the environment. Since the proportion of $^{14}C$ is substantially constant in the atmosphere, this is likewise the case in the organism, for as long as it is alive, since it absorbs this $^{14}C$ just as it absorbs $^{12}C$. The mean $^{14}C/^{12}C$ ratio is equal to $1.2 \times 10^{-12}$.

$^{12}C$ is stable, i.e. the number of $^{12}C$ atoms in a given sample is constant over time. $^{14}C$ is radioactive and each gram of carbon of a living being contains enough $^{14}C$ isotope to give 13.6 disintegrations per minute.

The half-life (or period) $T_{1/2}$, linked to the disintegration constant of $^{14}C$, is 5730 years. Taking this time into account, it is considered that the $^{14}C$ content is virtually constant from the extraction of the plant raw materials up to the manufacture of the final product.

At the present time, there are at least two different techniques for measuring the $^{14}C$ content of a sample:
 by liquid scintillation spectrometry
 by mass spectrometry: the sample is reduced to graphite or gaseous $CO_2$, and analyzed in a mass spectrometer. This technique uses an accelerator and a mass spectrometer to separate the $^{14}C$ ions from the $^{12}C$ ions and thus to determine the ratio of the two isotopes.

These methods for measuring the $^{14}C$ content of materials are described precisely in standards ASTM D 6866 (especially D 6866-06) and in standards ASTM D 7026 (especially 7026-04). The measuring method preferably used is mass spectrometry described in standard ASTM D6866-06 ("accelerator mass spectroscopy").

One subject of the invention is a bio-sourced glutaraldehyde compound with a mass content of $^{14}C$ such that the $^{14}C/^{12}C$ ratio is between $0.25 \times 10^{-12}$ and $1.2 \times 10^{-12}$. Preferably, its $^{14}C/^{12}C$ ratio is between $0.6 \times 10^{-12}$ and $1.2 \times 10^{-12}$ and more preferably between $0.9 \times 10^{-12}$ and $1.2 \times 10^{-12}$.

The $^{14}C/^{12}C$ ratio will depend on the manufacturing processes used according to the raw materials used, all or in part of non-fossil natural origin, or as a function of mixtures subsequently prepared. According to one embodiment of the invention, the $^{14}C/^{12}C$ ratio of the product is equal to $1.2 \times 10^{-12}$, all of the raw materials used being of non-fossil natural origin. This ratio cannot exceed $1.2 \times 10^{-12}$; if such were the case, this would imply that the operator has artificially introduced $^{14}C$ atoms into the glutaraldehyde compound.

The glutaraldehyde of the present invention differs from the glutaraldehyde of document WO 99/23088 in that it contains a mass content of $^{14}C$ such that the $^{14}C/^{12}C$ ratio is between $0.25 \times 10^{-12}$ and $1.2 \times 10^{-12}$. The technical effect of this characteristic is to reduce the environmental effects associated with the emission of greenhouse gases during the production of this compound. This bio-sourced glutaraldehyde thus meets the need, which was unsatisfied hitherto, of the novel concept of "green chemistry" within a more global context of sustainable development.

A subject of the invention is also processes for synthesizing the bio-sourced glutaraldehyde compound.

A first process consists schematically:
 in a first step, in subjecting a glycerol charge derived from the methanolysis of plant oils or animal fats to a dehydration reaction leading to acrolein according to the reaction $CH_2OH$—$CHOH$—$CH_2OH \rightarrow CH_2$=$CH$—$CHO + 2H_2O$ and then
 in a second step, in reacting the acrolein obtained with a vinyl alkyl ether, in general vinyl ethyl ether, according to a Diels-Alder cyclization reaction leading to the 2-alkoxy-3,4-dihydropyran whose structural formula is indicated below, and
 in a third step, in subjecting the 2-alkoxy-3,4-dihydropyran to a hydrolysis leading to glutaraldehyde.

The reaction scheme of steps 2 and 3 with vinyl ethyl ether is as follows:

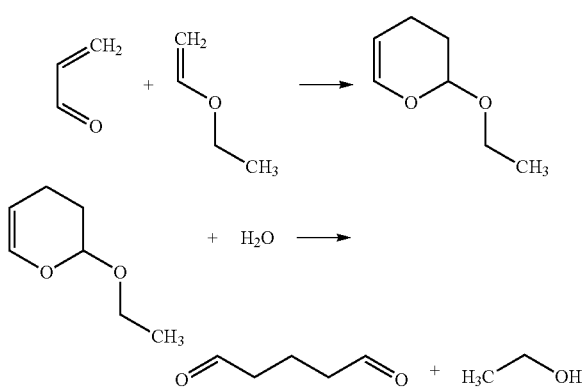

A second process consists schematically:

in a first step, in subjecting a glycerol charge derived from the methanolysis of plant or animal oils to a dehydration reaction leading to acrolein according to the reaction $CH_2OH\text{—}CHOH\text{—}CH_2OH \rightarrow CH_2\!=\!CH\text{—}CHO + 2H_2O$ and then in a second step, in reacting the acrolein obtained with a vinyl alkyl ether, synthesized from acetylene obtained from non-fossil natural materials according to known processes, according to a Diels-Alder cyclization reaction leading to the 2-alkoxy-3,4-dihydropyran, and in a third step, in subjecting the 2-alkoxy-3,4-dihydropyran to a hydrolysis leading to glutaraldehyde.

A third process consists schematically:

in a first step, in subjecting sugars containing 5 carbon atoms: pentoses (derived, for example, from hemicellulose) to a dehydration leading to furfural, and then in a second step, in totally hydrogenating the furfural, which leads to 1,5-pentanediol, and in a third step, in selectively oxidizing the diol to a dial.

It is understood that, according to the invention, these various processes may comprise other steps directed towards separating or purifying the constituents obtained during the various phases.

The charge used in the 1st step of the first process is glycerol—1,2,3-propanetriol—which is a coproduct formed during the methanolysis, or more generally alcoholyses, hydrolyses and saponifications, of plant oils or animal fats, the other coproduct being the methyl esters that are used especially as diesel and domestic fuel. The development of biofuels entails an increase in glycerol production according to this pathway in which glycerol represents about 10% by weight of the transformed oil.

Glycerol may be subjected beforehand to various purification treatments aimed at removing salts by distillation, by using ion-exchange resins or using a fluidized bed (French patent application 2 913 974) or by the purification and evaporation of glycerol, especially described by G. B. D'Souza in J. Am. Oil Chemists' Soc. November 1979 (Vol 56) 812A, by Steinberner U et al., in Fat. Sci. Technol. (1987), 89 Jahrgang No. 8, pp 297-303, and by Anderson D. D. et al. in Soaps and Detergents: A theoretical and Practical Review, Miami Beach Fla., Oct. 12-14, 1994, chapter 6 pp. 172-206. Ed: L Spitz, AOCS Press, Champaign.

Aqueous solutions of glycerol in which the concentration may vary within a wide range, for example from 20% to 99% by weight of glycerol, are generally used; preferably, solutions comprising from 30% to 80% by weight of glycerol are used.

The dehydration reaction:

$$CH_2OH\text{—}CHOH\text{—}CH_2OH \leftrightarrow CH_2OH\text{—}CH_2\text{—}CHO + H_2O \rightarrow CH_2\!=\!CH\text{—}CHO + 2H_2O$$

is an equilibrated reaction which is favored by a high temperature level. It is generally performed in the gas phase in the reactor in the presence of a catalyst, at a temperature ranging from 150° C. to 500° C., preferably between 250° C. and 350° C., and a pressure of between 1 and 5 bar. It may also be performed in the liquid phase. It may also be performed in the presence of oxygen or of a gas containing oxygen as described in patent applications WO 06/087 083 and WO 06/114 506. In these processes, the oxygen does not serve for oxidation, but in fact contributes towards decoking the catalyst (by burning the coke), which is not oxidant (in the sense that little acrylic acid and acetic acid are formed), but acidic, which rapidly become fouled, and thus towards prolonging its service life; in addition, it also contributes towards reducing the formation of interfering byproducts such as phenol, acetone and propanaldehyde, for example. As long as the temperature is not too high, there is no oxidation to acrylic acid.

The dehydration reaction of glycerol is generally performed on acidic solid catalysts. The catalysts that are suitable for use are homogeneous or multiphase materials, which are insoluble in the reaction medium and which have a Hammett acidity, denoted $H_0$, of less than +2. As indicated in U.S. Pat. No. 5,387,720, which makes reference to the article by K. Tanabe et al. in "Studies in Surface Science and Catalysis", Vol 51, 1989, chapters 1 and 2, the Hammett acidity is determined by amine titration using indicators or by adsorption of a base in the gaseous phase.

These catalysts may be chosen from natural or synthetic siliceous materials or acidic zeolites; mineral supports, such as oxides, covered with mono-, di-, tri- or polyacidic inorganic acids; oxides or mixed oxides, or alternatively heteropolyacids or salts of heteropolyacids.

These catalysts may generally consist of a heteropolyacid salt in which protons of the said heteropolyacid are exchanged with at least one cation chosen from elements belonging to groups I to XVI of the Periodic Table of the Elements, these heteropolyacid salts containing at least one element chosen from the group comprising W, Mo and V.

Among the mixed oxides, mention may be made particularly of those based on iron and phosphorus, those based on vanadium and phosphorus, those based on aluminum and phosphorus, boron and phosphorus, phosphorus or silicon and tungsten and those based on cesium, phosphorus and tungsten.

The catalysts are especially chosen from zeolites, Nafion® composites (based on sulfonic acids of fluoropolymers), chlorinated aluminas, acids and salts of phosphotungstic and/or silicotungstic acids, and various solids of metal oxide type such as tantalum oxide $Ta_2O_5$, niobium oxide $Nb_2O_5$, alumina $Al_2O_3$, titanium oxide $TiO_2$, zircon $ZrO_2$, tin oxide $SnO_2$, silica $SiO_2$ or silicoaluminate $SiO_2\text{—}Al_2O_3$, impregnated with acidic functions such as borate $BO_3$, sulfate $SO_4$, tungstate $WO_3$, phosphate $PO_4$, silicate $SiO_2$ or molybdate $MoO_3$, or a mixture of these compounds.

The preceding catalysts may also comprise a promoter such as Au, Ag, Cu, Pt, Rh, Pd, Ru, Sm, Ce, Yt, Sc, La, Zn, Mg, Fe, Co, Ni.

The preferred catalysts are phosphate-containing zircons, tungsten-containing zircons, siliceous zircons, titanium oxide or tin oxide impregnated with tungstate, silicotungstate or phosphotungstate, phosphate-containing aluminas or silicas, heteropolyacids or heteropolyacid salts, iron phosphates and iron phosphates comprising a promoter, vanadium-phosphorus mixed oxides, and also combinations of these various catalysts, or catalysts consisting of a support and an active phase comprising one of the abovementioned catalysts. The supports that may be suitable for use comprise, for example, alumina, silica, titanium oxide, zirconium oxide and niobium and tantalum oxides.

The acrolein derived from the dehydration reactor is in the form of a gaseous effluent, which should be treated before sending it into the second step to react with the vinyl alkyl ether. The treatment of the gaseous effluent is known and described in Ullmann's Encyclopedia volume A1 pages 149 et seq. devoted to acrolein and methacrolein. Another scheme is described in Les Techniques de l'Ingénieur J-6100 page 2. The treatment scheme on page 154 in Ullmann's Encyclopedia relates to acrolein obtained by oxidation of propylene, but, if the composition of the effluent is different—for example the ex-propylene effluent contains acrylic acid in substantial amount, contrary to the ex-glycerol effluent—the treatment scheme is globally the same. It will comprise at the reactor outlet a quench that abruptly lowers the temperature of the effluent in order to avoid polymerization reactions. It will then be subjected to washing with water to remove the heavy fractions of glycerol ethers, acetals and acids and the polymers that may have formed. It is then sent to an absorber to form with cold water an aqueous acrolein solution; the uncondensable compounds ($CO$, $CO_2$, $N_2$, Ar, residual oxygen, etc.) are then extracted at the top. The solution is then sent to a zone for desorption by stripping where the crude acrolein is separated from the aqueous phase, the latter phase being recycled into the absorption zone, the crude acrolein being subjected to two successive distillations for purification by head removal and then tail removal enabling the removal first of the light compounds (acetaldehyde, acetone, etc.) at the top of the first column and at the bottom removing an aqueous acrolein phase, and in the second column, the acrolein is separated at the top from the water which is removed at the bottom with the heavy compounds. Optionally, these last two columns may be combined as one, using lateral withdrawal to extract the acrolein, as is described in U.S. Pat. No. 6,515,187.

In the second step of the first process, a Diels-Alder reaction is performed according to the reaction scheme described previously.

The reaction is performed in the liquid phase in the presence of a solvent. To maximize the reaction yield relative to acrolein, the alkyl vinyl ether, generally methyl or ethyl vinyl ether, will be used in excess, this excess serving as reaction solvent. The reaction temperature is generally between 100 and 200° C. approximately, preferably between 120 and 190° C. and more preferably between 140 and 180° C. The reaction is performed at a pressure of between about 1 and 70 bar, preferably between 35 and 60 bar and more preferably between 40 and 55 bar. A polymerization inhibitor, for instance hydroquinone, butylhydroxytoluene or phenolphenothiazine, may be used to avoid the polymerization of the acrolein. The process may also be performed in the presence of the residual alcohol from the step that served to prepare the alkyl vinyl ether. The reaction may be performed under an inert atmosphere to prevent possible side reactions and to limit the risks of explosive reactions. The operating conditions of this reaction are well known to those skilled in the art. The reaction product, 2-alkoxy-3,4-dihydropyran, 2-methoxy-3,4-dihydropyran in the case of the preferred use of methyl vinyl ether, is extracted from the medium. Preferably, the pyran derivative is extracted by distillation, for example with a column operating under partial vacuum (less than 0.5 bar) and at a temperature of from 75 to 150° C., and it is possible to withdraw from the top the pyran derivative and from the bottom the heavy products derived from the preceding steps.

The 2-alkoxy-3,4-dihydropyran derived from the second step is then subjected to a hydrolysis in acidic medium, which leads, via opening of the ring, to the formation of glutaraldehyde according to the reaction scheme described previously.

It should be noted that the acrolein derived from the dehydration to of glycerol is particularly suited this process. The impurities present in the acrolein are mainly acetaldehyde and propanaldehyde. There are very few byproducts containing conjugated double bonds that may lead to other products via a Diels-Alder reaction. On the other hand, there is more propanaldehyde than in the acrolein derived from the oxidation of propylene, but in this case, it is not necessary to seek to separate them; the unreacted acrolein, just like the propanaldehyde, will in fact be automatically removed after the Diels Alder synthesis step.

The operating conditions of this hydrolysis are well known to those skilled in the art. The temperature will generally be between 50 and 150° C. and preferably between 75 and 125° C. The pressure will generally be between 0 and 7 bar and preferably between 0.3 and 4 bar and often below atmospheric pressure. The acidic medium will consist of a mineral acid, such as phosphoric acid, or an organic acid in aqueous solution. Specific conditions for the hydrolysis of the 2-alkoxy-3,4-dihydropyran are described by the company Daicel, for example in documents JP 59108734, JP 8040968 or JP 2000072707. At the end of the synthesis, the excess acid is optionally neutralized, for example with sodium hydroxide. The glutaraldehyde may then be purified by distillation.

The glutaraldehyde obtained via this process has a $^{14}C/^{12}C$ ratio of about $0.7 \times 10^{-12}$.

The second process is similar to the first and differs therefrom by the nature of the alkyl vinyl ether used during the synthesis. This alkyl vinyl ether is synthesized by reaction of a light alcohol with acetylene obtained from non-fossil natural raw materials.

The non-fossil natural raw materials that may be used for synthesizing acetylene by means of industrially developed processes are well known. The renewable raw material(s) that may be used in the process according to the invention may be chosen from wood in the form of wood charcoal or wood tars, especially pine tar, biomass in the form of straw, cellulose or lignin which is subjected to a pyrolysis from which are recovered the heavy residues (or pitch) rich in carbon and finally biomass treated by fermentation for obtaining methane (methanization). These carbon sources participating in the reaction mechanisms are either solid (wood charcoal) or "liquid" (pyrolysis residues or tars); by "liquid" it should be understood that, when heated, these charges pass without decomposition from the solid state to the liquid state, or gaseous (essentially methane).

The various processes for manufacturing acetylene from hydrocarbons are well known and may be used for the treatment of charges derived from the raw materials mentioned above, depending on the nature and origin of said hydrocarbon-based charges. They may be classified in two categories: chemical processes, which are the older ones, used for transforming coal, are based on the reduction of calcium oxide to calcium carbide, and thermodynamic processes are based on the thermodynamic properties of acetylene versus that of the other hydrocarbons at very high temperature, i.e. T>1400° K.

The method for manufacturing acetylene chemically according to the process of the invention consists first in reducing calcium oxide with carbon obtained from non-fossil natural raw materials, mainly wood charcoal, or any charcoal derived from the pyrolysis of a biomass-based product, such as charcoals derived from sugars, cellulose or straw to form calcium carbide, and then in hydrolyzing it to form acetylene according to the following reaction process:

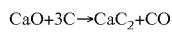

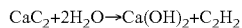

The non-fossil natural raw materials that may be used to form the charcoal that is capable of reacting with calcium oxide and the processes for manufacturing them are well known. The renewable raw materials that may be used in the process according to the invention may be chosen, for example, from wood charcoal, wood tars, especially from pine, or straw, and heavy pyrolysis residues of biomass, especially of straw.

Wood charcoal may be obtained via any well-known conventional method and especially by controlled and partial carbonization.

Wood and agricultural products in the broad sense of the term, i.e. biomass, may be used as fuels in installations in which they provide heat by combustion. Beyond the environmental problems posed by their various constituents that risk passing into the atmosphere, this type of use is not optimal. This is why one route for treating these raw materials, which had for that matter been known for a long time, but for other purposes, is used. This treatment is pyrolysis, which consists in heating these raw materials in the absence of air in order to avoid combustion. During the rise in temperature of the biomass, the removal of water is observed in a first stage at about 100-110° C., followed by the start of carbonization with evolution of the light compounds, comprising methane, some of which may be condensed. Continuation of the operation with raising of the temperature leads to the formation within the pyrolysis reactor of liquid heavy residues (wood tars) and also wood charcoal. The amounts of pyrolysis residues and of wood charcoal will depend on the one hand on the nature of the biomass, and on the other hand on the operating conditions of this pyrolysis as regards the reaction temperature and time.

The reduction of calcium oxide with carbon to form calcium carbide is generally performed in a closed electric oven equipped with three electrodes and lined on the inside with refractory bricks.

The reagents are introduced into the oven, the temperature of which is generally between 2200° C. and 2300° C. at atmospheric pressure.

The calcium carbide is obtained in molten form and is extracted at the bottom of the oven. After cooling and forming, the calcium carbide is subjected to a hydrolysis step. This hydrolysis step may be performed via a wet route or via a dry route, depending on whether the residual lime is extracted in the form of a milk or in the form of hydrated lime without excess water.

The hydrolysis of the calcium carbide to form acetylene must be performed with caution to avoid decomposition of the acetylene.

After cooling and condensation of the majority of the water, the acetylene is then purified.

The production of acetylene from solid fuels such as charcoals is described in the publication Procédés de pétrochimie, Caractéristiques techniques et économiques, 1985, 2nd edition, volume 1, published by Technic, on pages 346 to 349.

According to the other "thermodynamic" route, acetylene is produced with hydrocarbons obtained from wood or from biomass either in liquid form or in gaseous form, via a process comprising a step of energy transfer to said hydrocarbon(s), followed by a quenching step.

The production of acetylene from one or more of these hydrocarbons is based on the thermodynamic properties of acetylene. Common paraffins and olefins are more stable than acetylene at normal temperatures. When the temperature increases to reach 1400° K, acetylene becomes relatively more stable than the other hydrocarbons. However, at this temperature, since acetylene is unstable with respect to its elements C and $H_2$, it is necessary, in order to form a lot of acetylene, to very rapidly bring the reaction medium to a high temperature by energy transfer, and also subsequently to perform extremely rapid quenching of the medium in order to avoid decomposition of the acetylene. The study of the theory of these processes is described in Kirk-Othmer's Encyclopedia, volume 13, pages 780 to 784.

The energy transfer may take place by direct heat transfer using an electric arc or a plasma, or alternatively by indirect heat transfer by means of contact masses or water vapor, or alternatively via the autothermal process in which the heat required for the cracking reaction is supplied by combustion of part of the charge.

These various processes have been the subject of major industrial developments.

Among the "direct heat transfer" techniques, processes using an electric arc, such as the Hüls process, and thermal "plasma" processes with the two variants, arc ionization of a gas or passage of a high-frequency electric current in a solenoid surrounding the reaction space, such as the Hoechst and Hüls processes using hydrogen as gas, may be distinguished.

Among the indirect heat transfer processes, mention may be made of the Wulff process and the Kureha process.

In an autothermal process, the combustion of part of the charge supplies the heat required for the cracking reaction of the rest of this charge. These are especially the BASF, Montecatini and Hoechst processes.

These various thermodynamic processes are described in the book Procédés de pétrochimie cited above on pages 349 to 367 and also in Kirk-Othmer's Encyclopedia cited above on pages 784 to 799. They may also be applied to liquid and gaseous hydrocarbon-based charges.

These various processes may be used with charges such as "liquid" pyrolysis residues, or certain gaseous fractions containing methane obtained during this pyrolysis.

The production of methane from biomass is known. Thus, methane may be obtained from biogas. Biogas is the gas produced by the fermentation of animal and/or plant organic matter in the absence of oxygen.

This fermentation, also known as methanization, takes place naturally or spontaneously in waste disposal sites containing organic waste, but may be performed in digesters, for example to treat organic or agricultural waste, pig slurry, etc. Preferably, biomass containing animal dejecta that serves as a nitrogen input necessary for the growth of the microorganisms that perform the fermentation of the biomass to methane is used.

Biogas is composed essentially of methane and carbon dioxide, which may be removed by washing the biogas using a basic aqueous solution, or alternatively with water under pressure or by absorption in a solvent such as methanol. It is possible via this route to obtain pure methane of constant quality.

Methanization processes are well known to those skilled in the art. Reference may be made in particular to the article Review of Current Status of Anaerobic Digestion Technology for Treatment of Municipal Solid Waste, November 1998, RISE-AT.

A problem posed by the use of acetylene synthesized with hydrocarbons derived from biomass lies in the presence of impurities inherent in the biomass, namely sulfur, phosphorus, and silicon. Specifically, biomass contains sulfur compounds such as sulfur-bearing amino acids (cysteine, methionine, etc.) and phosphorus compounds such as adenosine triphosphate. In the course of the transformation of biomass, these compounds will lead to a production of hydrogen sulfide gas and phosphine. Lignocellulosic biomass also contains, for example, silica. In certain cases, the silica content may be very high and up to, for example, 20% by weight in rice straw. It is desirable to eliminate these impurities by pretreatment or to select the biomass used. Thus, sulfur compounds can be eliminated in part by avoiding the introduction of proteins into the process chain, or by treating the carbon-based matter prior to the carbide manufacturing step with aqueous hydrogen peroxide solution, in order to extract the sulfur molecules in the form of sulfones, sulfoxides or sulfates.

It should be noted that the process starting with wood charcoal, on account of the prior elimination of the majority of the other constituents of the biomass, makes it possible to limit the formation of impurities.

The vinyl alkyl ether is synthesized in a known manner by reaction in the liquid phase in the presence of a strong base, between the light alcohol, generally methanol, and acetylene manufactured according to one of the processes mentioned above. The other steps of the overall process are identical to those of the first process described previously.

The glutaraldehyde obtained according to this process has a $^{14}C/^{12}C$ ratio of greater than $1.1 \times 10^{-12}$.

The third process consists:
- in a first step, in subjecting sugars containing 5 carbon atoms: pentoses derived, for example, from hemicellulose, to a dehydration leading to furfural, and then
- in a second step, in totally hydrogenating the furfural, which leads to 1,5-pentanediol, and
- in a third step, in selectively oxidizing the diol to dial.

The first step is performed under the following conditions. Pentose-rich agricultural waste is used as raw material. The hemicelluloses that are present in lignocellulose-based materials consist mainly of pentoses. The most suitable raw materials are, for example, corn husks, the envelopes of cotton seeds or oat seeds, sugarcane bagasse, and the envelopes of rice grains, woodchips or straw.

The depolymerization of hemicellulose leads to xylose, which is transformed by cyclodehydration into furfural, according to the following reaction mechanism:

Hemicellulose + H₃O⁺ ⟶

CHO—(CHOH)₃—CH₂OH ⟶ Furfural + 3 H₂O

Hemicellulose + H₃O⁺ ⟶

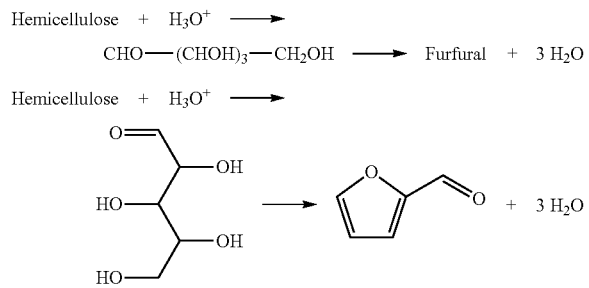

The raw material is treated, for example, by acidic hydrolysis, for example in the presence of sulfuric acid, at a temperature of about 180° C., preferably at a temperature below 190° C. The reactors are heated with superheated steam. The furfural yield is generally about 50%. A description of the processes used for this step is given in the report PERP, No. 147, Chemicals from wood wastes and pulping residues, June 1982 and in the report CEH Product Review, Furfural, March 2008.

During the second step, the furfural is hydrogenated to give 1,5-pentanediol. This step will generally be performed as several sub-steps. Specifically, in a first variant, tetrahydrofurfuryl alcohol (THFA) will be synthesized,
either directly according to the following reaction:

Furfural + 3H₂ ⟶ THFA

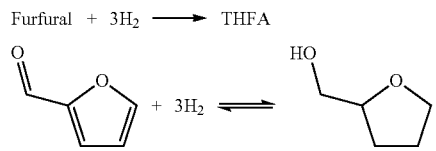

or by passing through an intermediate stage according to the two reactions:

Furfural + H₂ ⟶ Furfuryl alcohol

Furfuryl alcohol + 2 H₂ ⟶ THFA

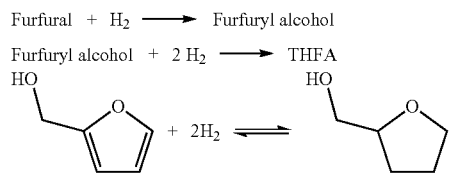

The direct synthesis may be performed in the presence of catalysts using metals such as palladium, ruthenium, rhenium and nickel, optionally combined with copper, deposited on a support such as a silica-alumina. It will be particularly advantageous to use an Ni—Cu or Ru—Cu mixed catalyst on support. The reaction will be performed in the liquid phase in an alcohol solvent such as methanol.

For the indirect synthesis performed in the liquid phase, a supported copper catalyst or a copper chromite may be used for the first phase leading to furfuryl alcohol, and then a nickel or ruthenium supported catalyst or a nickel-doped chromium catalyst for the second phase leading to THFA.

According to a second variant, the hydrogenation of the first phase may be performed in the gaseous phase in the presence of a copper and magnesium mixed oxide catalyst to obtain THFA.

The hydrogenation of furfural has been the subject of a study by Nadine Merat et al. published in J. Chem. Tech. Biotechnol, 1990, 48, pages 145-159.

The final hydrogenation leading to 1,5-pentanediol according to the reaction:

THFA+H₂→CH₂OH—(CH₂)₃—CH₂OH is performed in the presence of a catalyst based on copper and chromium mixed oxide at a pressure of between 20 and 40 bar at a temperature of between 200 and 300° C.

The third and final oxidation step of pentanediol to pentanedial according to the reaction:

CH₂OH—(CH₂)₃—CH₂OH+O₂→CHO—(CH₂)₃—CHO+2H₂O is performed in the liquid phase in the presence of a selective oxidation catalyst. Among the reagents most commonly used, mention may be made of the Collins reagent (chromium trioxide, pyridine, dichloromethane), the Corey reagent (pyridinium chlorochromate) or the Swern reagent (oxalyl chloride, dimethyl sulfoxide, triethylamine). The reaction is generally performed at room temperature and atmospheric pressure in the presence of an excess of the oxidation reagent.

The oxidation of alcohols to aldehydes forms the subject of a chapter in Advanced Organic Chemistry, reactions, mechanisms and structure, Jerry March, 4th ed., Wiley-Interscience publication, 1992, pp. 1167-1171.

This reaction may in particular be performed in the liquid phase according to the following operating conditions:
- ruthenium catalyst (for example Ru-100 from JM), at a temperature of 25 to 110° C., at atmospheric pressure, in acetonitrile, toluene or dichloromethane solvent medium, for example, by oxidation with molecular oxygen (with air or with oxygen).
- Pt, Pd and/or Ru catalyst supported on charcoal or alumina, at a temperature of 30 to 70° C., at a pressure of 1 to 3 bar abs, in toluene or hydrocarbons, by oxidation with molecular oxygen (for example air or oxygen).

The glutaraldehyde obtained according to this process has a $^{14}C/^{12}C$ ratio of greater than $1.1 \times 10^{-12}$.

The invention claimed is:

1. A process for manufacturing a bio-sourced glutaraldehyde compound with a mass content of $^{14}C$ such that the $^{14}C/^{12}C$ ratio is between $0.25 \times 10^{-12}$ and $1.2 \times 10^{-12}$ comprising, first, subjecting a glycerol charge derived from methanolysis of plant oils or animal fats to a dehydration reaction leading to acrolein, according to the reaction $CH_2OH—CHOH—CH_2OH \rightarrow CH_2=CH—CHO+2H_2O$, and then, second, reacting the acrolein obtained with a vinyl alkyl ether synthesized by reacting a light alcohol with acetylene obtained from non-fossil natural raw materials, in a Diels-Alder cyclization reaction leading to 2-alkoxy-3,4-dihydropyran and, third, subjecting the 2-alkoxy-3,4-dihydropyran to a hydrolysis leading to glutaraldehyde.

2. The process as claimed in claim 1, wherein the dehydration is performed in gas phase in a reactor in the presence of a solid catalyst, which is insoluble in the reaction medium, and is a homogeneous or multiphase material with a Hammett acidity $H_0$ of less than +2, at a temperature ranging from 150° C. to 500° C., and at a pressure of between 1 and 5 bar.

3. The process as claimed in claim 1, wherein reaction of acrolein with a vinyl alkyl ether, according to a Diels-Alder cyclization reaction leading to the 2-alkoxy-3,4-dihydropyran, is performed in liquid phase in the presence of a solvent at a temperature of between 100 and 200° C. and under a pressure of between 1 and 70 bar.

4. The process as claimed in claim 3, wherein the solvent is the alkyl vinyl ether of the reaction used in excess.

5. The process as claimed in claim 1, wherein hydrolysis is performed in acidic medium at a temperature of between 50 and 150° C. and at a pressure of between 0 and 7 bar.

6. The process as claimed in claim 5, wherein the acidic medium comprises a mineral acid, or an organic acid in aqueous solution.

7. The process as claimed in claim 1, with a mass content of $^{14}C$ such that the $^{14}C/^{12}C$ ratio is between $0.6 \times 10^{-12}$ and $1.2 \times 10^{-12}$.

8. The process as claimed in claim 1, with a mass content of $^{14}C$ such that the $^{14}C/^{12}C$ ratio is between $0.9 \times 10^{-12}$ and $1.2 \times 10^{-12}$.

9. A process for manufacturing a bio-sourced glutaraldehyde compound with a mass content of $^{14}C$ such that the $^{14}C/^{12}C$ ratio is between $0.25 \times 10^{-12}$ and $1.2 \times 10^{-12}$ comprising first, subjecting sugars containing 5 carbon atoms to a dehydration leading to furfural and then, second, totally hydrogenating the furfural to obtain 1,5-pentanediol and, third, selectively oxidizing the diol to dial.

10. The process as claimed in claim 9, wherein dehydration is an acidic hydrolysis at a temperature of about 180° C. this temperature being obtained with superheated steam.

11. The process as claimed in claim 9, wherein hydrogenation comprises, first, hydrogenating furfural to tetrahydrofurfuryl alcohol (THFA), and then hydrogenating the latter to 1,5-pentanediol.

12. The process as claimed in claim 11, wherein the hydrogenation of furfural to tetrahydrofurfuryl alcohol (THFA) is performed in the presence of catalysts based on palladium, ruthenium, rhenium and nickel, optionally combined with copper, deposited on a support in liquid phase in an alcohol solvent.

13. The process as claimed in claim 11, wherein the hydrogenation of furfural is performed by passing via an intermediate stage with hydrogenation of the furfural to furfuryl alcohol, and then that of the furfuryl alcohol to tetrahydrofurfuryl alcohol (THFA), the first hydrogenation leading to furfuryl alcohol, performed in liquid phase, optionally being performed in the presence of a supported copper catalyst or a copper chromite, and the second hydrogenation leading to THFA, optionally being performed in the presence of a nickel or ruthenium supported catalyst or a nickel-doped chromium catalyst.

14. The process as claimed in claim 11, wherein final hydrogenation of tetrahydrofurfuryl alcohol to pentanediol is performed in the presence of a catalyst based on copper and chromium mixed oxide at a pressure of between 20 and 40 bar and at a temperature of between 200 and 300° C.

15. The process as claimed in claim 9, wherein oxidation is performed in the liquid phase in the presence of a selective oxidation catalyst.

16. The process according to claim 15, wherein the catalyst is a Collins reagent that is chromium trioxide, pyridine or dichloromethane, a Corey reagent that is pyridinium chlorochromate or a Swern reagent, that is oxalyl chloride, dimethyl sulfoxide, or triethylamine.

17. The process according to claim 15, wherein the support is silica-alumina.

18. The process according to claim 6, wherein medium comprises phosphoric acid.

19. The process according to claim 9, wherein the sugars comprise pentoses.

20. The process according to claim 19, wherein the pentoses are derived from hemicellulose.

* * * * *